(12) United States Patent
Lynch et al.

(10) Patent No.: US 9,464,098 B2
(45) Date of Patent: Oct. 11, 2016

(54) SUBSTITUTED TRIAZOLE BORONIC ACID COMPOUNDS

(71) Applicants: Hoffmann-La Roche Inc., Nutley, NJ (US); F. HOFFMANN-LA ROCHE AG, Basel (CH)

(72) Inventors: Stephen M. Lynch, Westfield, NJ (US); Werner Neidhart, Basel (CH); Jean-Marc Plancher, Hagenthal-le-Bas (FR); Tanja Schulz-Gasch, Ziefen (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/646,782

(22) PCT Filed: Nov. 29, 2013

(86) PCT No.: PCT/EP2013/075031
§ 371 (c)(1),
(2) Date: May 22, 2015

(87) PCT Pub. No.: WO2014/086664
PCT Pub. Date: Jun. 12, 2014

(65) Prior Publication Data
US 2015/0329565 A1   Nov. 19, 2015

Related U.S. Application Data

(60) Provisional application No. 61/732,459, filed on Dec. 3, 2012.

(51) Int. Cl.
*A61K 31/4192* (2006.01)
*C07F 5/02* (2006.01)

(52) U.S. Cl.
CPC .................... *C07F 5/025* (2013.01)

(58) Field of Classification Search
USPC ................... 514/64, 359, 741, 383
See application file for complete search history.

(56) References Cited

U.S. PATENT DOCUMENTS

2011/0172186 A1*   7/2011  Behnke ................. A61K 31/69
                                                          514/64

FOREIGN PATENT DOCUMENTS

| WO | 2011094426 | 8/2011 |
| WO | 2012078540 | 6/2012 |
| WO | 2013092979 | 6/2013 |

OTHER PUBLICATIONS

The Japanese Office Action, issued on May 24, 2016, in the corresponding Japanese Application No. 2015-545745.

\* cited by examiner

*Primary Examiner* — Pancham Bakshi

(57) ABSTRACT

The invention is concerned with the compounds of formula (I) and pharmaceutically acceptable salts thereof. In addition, the present invention relates to methods of manufacturing and using the compounds of formula I as well as pharmaceutical compositions containing such compounds. The compounds of formula I are LMP7 inhibitors and may be useful in treating associated inflammatory diseases and disorders such as, for example, rheumatoid arthritis, lupus and irritable bowel disease.

(I)

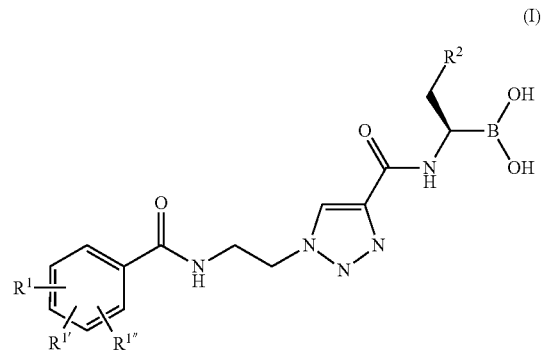

8 Claims, No Drawings

SUBSTITUTED TRIAZOLE BORONIC ACID COMPOUNDS

CROSS-REFERENCE TO RELATED APPLICATIONS

This application is a National Stage Application of PCT/EP2013/075031 filed Nov. 29, 2013, which claims priority from U.S. Provisional Patent Application No. 61/732,459, filed on Dec. 3, 2012. The priority of both said PCT and U.S. Provisional Patent Application are claimed. Each of the prior mentioned applications is hereby incorporated by reference herein in its entirety.

FIELD OF THE INVENTION

The present invention relates to organic compounds useful for therapy and/or prophylaxis in a mammal of an inflammatory disease or disorder, and in particular to substituted triazole boronic acid compounds for the treatment of rheumatoid arthritis, lupus and irritable bowel disease (IBD), their manufacture, pharmaceutical compositions containing them and their use as LMP7 inhibitors.

BACKGROUND OF THE INVENTION

LMP7 is an essential component of the immunoproteasome, mainly expressed in immune cells such as T/B lymphocytes and monocytes, as well as non-immune cells that have exposed to inflammatory cytokines, including IFN-γ and TNFα. Immunoproteasome plays an essential role in generation of antigenic peptide repertoire and shaping MHC class I restricted CD8+ T cell response. Moebius J. et al. *European Journal of Immunology*. 2010; Basler, M. et al. *Journal of Immunology*. 2004. 3925-34. Emerging data suggested that LMP7 also regulate inflammatory cytokine production and immune cell functions beyond the regulation of MHC class I mediated antigen presentation.

A small molecule LMP7 inhibitor, PR-957, has been shown to potently block Th1/17 differentiation, B cell effector functions and production of inflammatory cytokines (IL-6, TNF-α, IL-23). Muchamuel T. et al. *Natural Medicine*. 2009. 15, 781-787; Basler M. et al. *Journal of Immunology*. 2010, 634-41.

In addition, LMP7 blockade with PR-957 has been demonstrated to produce therapeutic benefits in several preclinical autoimmune disease models. First, PR-957 was demonstrated to significantly decrease disease score in mouse CAIA and CIA arthritis models, with hallmarks of significantly reduced inflammation and bone erosion. Muchamuel T. et al. *Natural Medicine*. 2009. 15, 781-787. In addition, PR-957 reduced plasma cells numbers and levels of anti-dsDNA IgG in MRL/lpr lupus-prone mice model, and prevented disease progression in these mice. Ichikawa H T, et al. *Arthritis & Rheumatism*. 2012. 64, 493-503. Furthermore, PR-957 reduced inflammation and tissue destruction in a DSS-induced colitis model in mice. Basler M. et al. *Journal of Immunology*. 2010, 634-41. Lastly, LMP7 knock-out mice had also been shown to be protected from disease in IBD models. Schmidt N. et al. *Gut* 2010. 896-906.

Taken together, data strongly suggests that LMP7 activity is closely related to the functions of B/T lymphocytes and production of inflammatory cytokines, all of which are clinically validated targets/pathways in the pathogenesis of rheumatoid arthritis, lupus and IBD. Thus, existing data have provided strong rationale for targeting LMP7 for autoimmune disease indications. Due to potential liability with long term usage of a covalent inhibitor in chronic diseases like autoimmunity, a covalent reversible or non-covalent small molecule LMP7 inhibitor is highly desired for autoimmune disease indications.

SUMMARY OF THE INVENTION

The invention provides for a compound of formula (I):

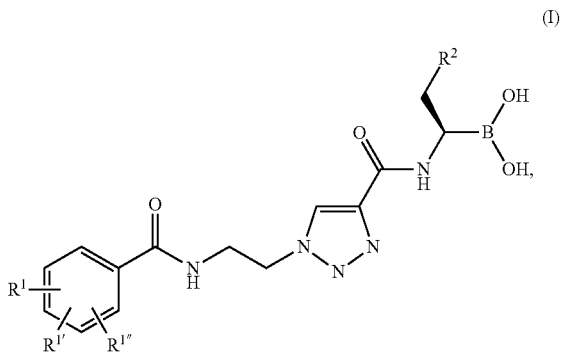

wherein:
$R^1$, $R^{1'}$ and $R^{1''}$, independently of each other, are hydrogen, alkoxy, halogen or —$CF_3$; and
$R^2$ is $C_{1-7}$ alkyl or phenyl,
or a pharmaceutically acceptable salt thereof.

The invention also provides for pharmaceutical compositions comprising the compounds, methods of using the compounds and methods of preparing the compounds.

All documents cited to or relied upon are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the R variables of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "$C_{1-7}$ alkyl substituted by halogen" refers to the fact that one or more hydrogen atoms of a $C_{1-7}$ alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms, more particularly 1 to 7 carbon atoms.

The term "$C_{1-7}$ alkyl" refers to an alkyl moiety having 1 to 7 carbon atoms. Examples of $C_{1-7}$ alkyls include methyl, ethyl, propyl, isopropyl, butyl, isobutyl, sec-butyl and tert-butyl.

The term "alkoxy" denotes a group of the formula —O—R', wherein R' is an alkyl group. Examples of alkoxy moieties include methoxy, ethoxy, isopropoxy, and tert-butoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The terms "halo", "halogen" and "halide", which may be used interchangeably, refer to a substituent fluoro, chloro, bromo, or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place as a consequence of hygroscopic properties of an initially anhydrous compound of formula I (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

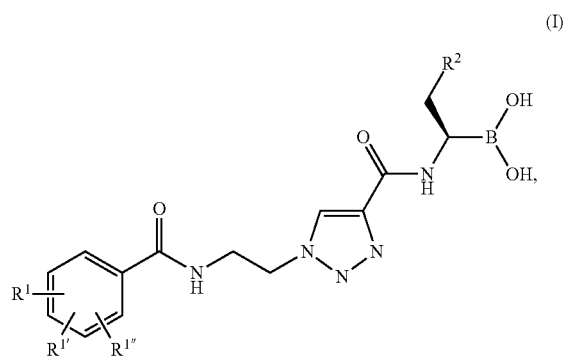

wherein:

$R^1$, $R^{1'}$ and $R^{1''}$, independently of each other, are hydrogen, alkoxy, halogen or —$CF_3$; and $R^2$ is $C_{1-7}$ alkyl or phenyl, or a pharmaceutically acceptable salt thereof.

In another embodiment, the present invention provides for compounds of formula (I) wherein $R^1$, $R^{1'}$ and $R^{1''}$, independently of each other, are hydrogen, methoxy, fluorine or —$CF_3$.

In another embodiment, the present invention provides for compounds of formula (I) wherein one of $R^1$, $R^{1'}$ and $R^{1''}$ hydrogen and the other two, independently of each other, are alkoxy, halogen or —$CF_3$.

In another embodiment, the present invention provides for compounds of formula (I) wherein one of $R^1$, $R^{1'}$ and $R^{1''}$ hydrogen and the other two, independently of each other, are methoxy, fluorine or —$CF_3$.

In another embodiment, the present invention provides for compounds of formula (I) wherein one of $R^1$, $R^{1'}$ and $R^{1''}$ methoxy in ortho, one is methoxy in meta and one is methoxy in para.

In another embodiment, the present invention provides for compounds of formula (I) wherein one of $R^1$, $R^{1'}$ and $R^{1''}$ fluoro in ortho, one is hydrogen in meta and one is —$CF_3$ in para.

In another embodiment, the present invention provides for compounds of formula (I) wherein one of $R^1$, $R^{1'}$ and $R^{1''}$ methoxy in ortho, one is hydrogen in meta and one is —$CF_3$ in para. In another embodiment, the present invention provides for compounds of formula (I) wherein $R^2$ is methyl.

In another embodiment, the present invention provides for compounds of formula (I) wherein $R^2$ is phenyl.

In another embodiment, the present invention provides for compounds of formula (I) wherein the compound is:
(R)-3-Methyl-1-(1-(2-(2,3,4-trimethoxybenzamido)ethyl)-1H-1,2,3-triazole-4-carboxamido)butylboronic acid;
(R)-2-Phenyl-1-(1-(2-(2,3,4-trimethoxybenzamido)ethyl)-1H-1,2,3-triazole-4-carboxamido)ethylboronic acid;
(R)-1-(1-(2-(2-Fluoro-4-(trifluoromethyl)benzamido)ethyl)-1H-1,2,3-triazole-4-carboxamido)-2-phenylethylboronic acid; or
(R)-1-(1-(2-(2-Methoxy-4-(trifluoromethyl)benzamido)ethyl)-1H-1,2,3-triazole-4-carboxamido)-2-phenylethylboronic acid; or
pharmaceutically acceptable salts thereof.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of an inflammatory disease or disorder selected from rheumatoid arthritis, lupus and irritable bowel disease.

In another embodiment, the invention provides for the use of a compound according to formula (I) for the preparation of a medicament for the treatment or prophylaxis of an inflammatory disease or disorder selected from rheumatoid arthritis, lupus and irritable bowel disease.

In another embodiment, the invention provides for a compound according to formula (I) for the treatment or prophylaxis of an inflammatory disease or disorder selected from rheumatoid arthritis, lupus and irritable bowel disease.

In another embodiment, the invention provides for a method for treating an inflammatory disease or disorder selected from rheumatoid arthritis, lupus and irritable bowel disease (IBD), comprising the step of administering a therapeutically effective amount of a compound according to formula (I) to a subject in need thereof.

In another embodiment, provided is an invention as hereinbefore described.

Synthesis

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in the Schemes below.

Scheme 1

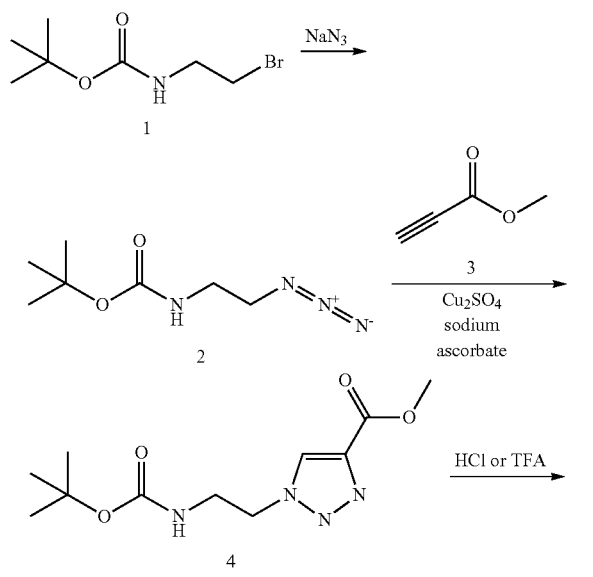

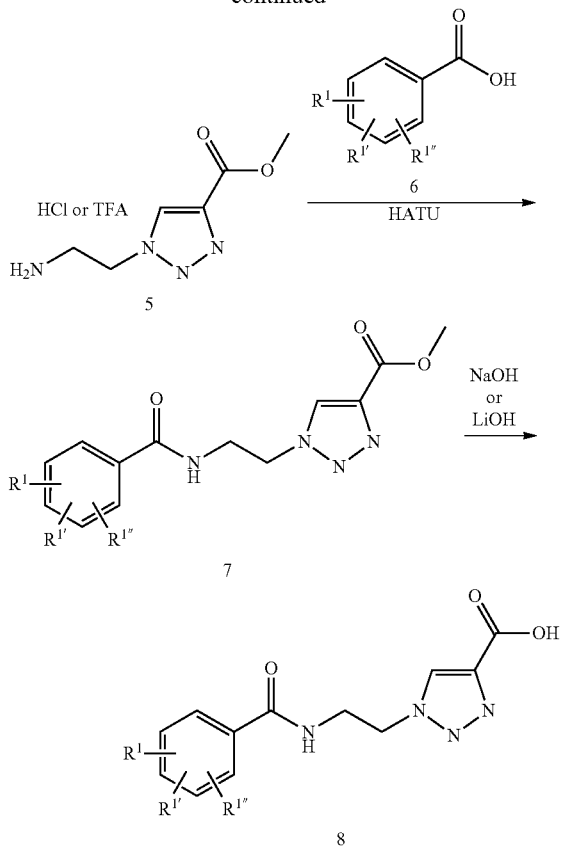

As seen in Scheme 1, bromide 1 can be converted to azide 2 using sodium azide then can be reacted with methyl propiolate 3 in the presence of copper (II) sulfate and sodium ascorbate to afford 1,2,3-triazole 4 in a regioselective manner. The N-Boc protecting group can be removed using a strong acid such as HCl or TFA. The resultant amine salt 5 can be coupled with variably substituted acids 6 using an activating reagent such as HATU to provide ester 7. Hydrolysis under basic conditions affords acid 8. $R^1$, $R^{1'}$ and $R^{1''}$, independently of each other, can be, for example hydrogen, alkoxy, halogen or —$CF_3$. $R^2$ can be, for example, $C_{1-7}$ alkyl or phenyl.

Scheme 2

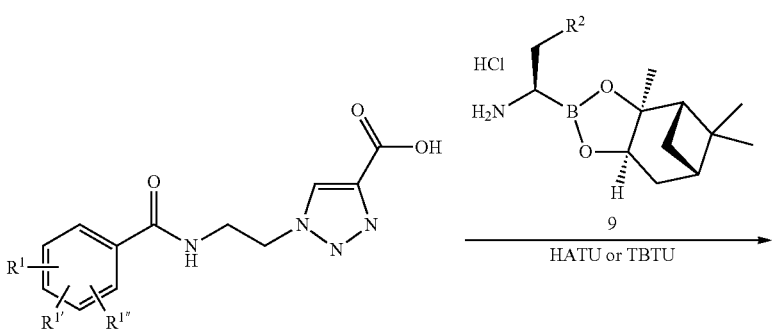

-continued

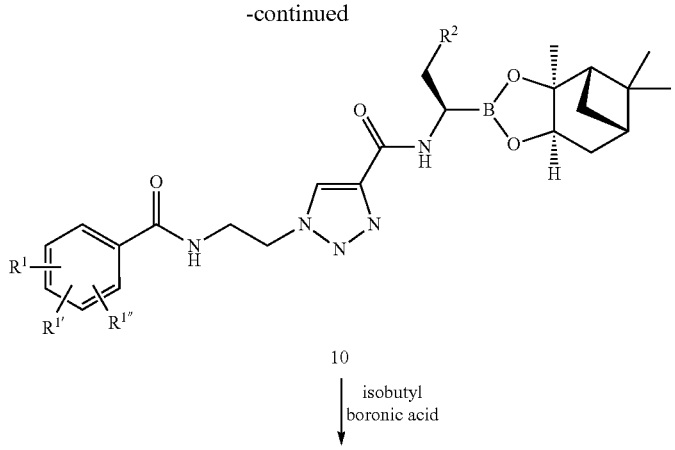

10

| isobutyl boronic acid

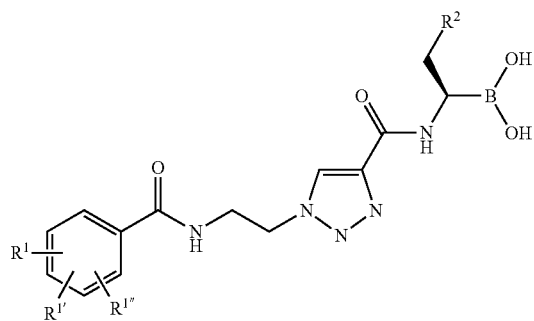

11

According to Scheme 2, acid 8 can be coupled with variably substituted pinanediol boronic acid esters 9 using an activating reagent such as HATU or TBTU to afford triazole 10. Ester exchange with isobutyl boronic acid can provide the desired boronic acid 11. $R^1$, $R^{1'}$ and $R^{1''}$, independently of each other, can be, for example hydrogen, alkoxy, halogen or —$CF_3$. $R^2$ can be, for example, $C_{1-7}$ alkyl or phenyl.

EXAMPLES

Although certain exemplary embodiments are depicted and described herein, the compounds of the present invention can be prepared using appropriate starting materials according to the methods described generally herein and/or by methods available to one of ordinary skill in the art. All reactions involving air-sensitive reagents were performed under an inert atmosphere. Reagents were used as received from commercial suppliers unless otherwise noted.

Intermediate 1

1-(2-Amino-ethyl)-1H-[1,2,3]triazole-4-carboxylic acid methyl ester hydrochloride 2-(Boc-amino)ethyl bromide (5.0 g, 22.3 mmol) was dissolved in 50 ml DMF and sodium azide (1.6 g, 24.5 mmol) was added. The reaction mixture was stirred at 80° C. for 12 h. The reaction mixture was diluted with diethyl ether (200 ml) and washed with water (3×) and brine (2×). The organic phase was dried over sodium sulfate and concentrated under reduced pressure to afford 3.9 g (94%) (2-azido-ethyl)-carbamic acid tert-butyl ester as a colorless viscous oil. GC/MS: $(M+H)^+=187.191$.

(2-Azido-ethyl)-carbamic acid tert-butyl ester (3.9 g, 20.8 mmol) and methyl propiolate (3.5 g, 3.71 ml, 41.7 mmol) were dissolved in 50 ml tert-butanol. A 1.0 M aq. solution of copper(II) sulfate pentahydrate (4.17 ml, 4.17 mmol) was added followed by a 1.0 M aq. solution of sodium ascorbate (16.7 ml, 16.7 mmol). The reaction mixture was stirred at room temperature for 60 h. The reaction mixture was quenched with 150 ml water and extracted with EtOAc (3×80 ml). The organic layers were combined, dried over sodium sulfate, filtered and concentrated. The residue was chromatographed over 70 g silica gel with EtOAc/dichloromethane (gradient: 0-40% EtOAc). All fractions containing product were combined and concentrated to afford 3.2 g (57%) 1-(2-tert-butoxycarbonylamino-ethyl)-1H-[1,2,3]triazole-4-carboxylic acid methyl ester as an off-white solid. LC/HR-MS: $(M+H)^+=271.1401$.

1-(2-tert-Butoxycarbonylamino-ethyl)-1H-[1,2,3]triazole-4-carboxylic acid methyl ester (1.75 g, 6.47 mmol) was dissolved in 4N HCl in dioxane (16.2 ml, 64.7 mmol) and stirred at room temperature for 3 h. The solvent was evaporated to afford 1.32 g (99%) 1-(2-amino-ethyl)-1H-[1,2,3]triazole-4-carboxylic acid methyl ester hydrochloride as a white solid.

Example 1

(R)-3-Methyl-1-(1-(2-(2,3,4-trimethoxybenzamido)ethyl)-1H-1,2,3-triazole-4-carboxamido)butylboronic acid

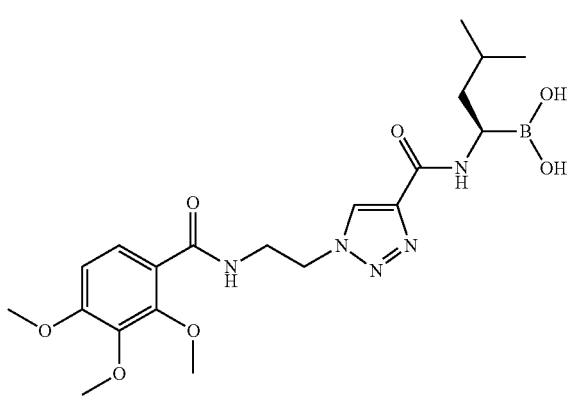 [SMILES: COc1ccc(C(=O)NCCn2cc(C(=O)N[C@@H](CC(C)C)B(O)O)nn2)c(OC)c1OC]

A flask was charged with 2,3,4-trimethoxybenzoic acid (1.29 g, 6.08 mmol), 57 ml N,N-dimethylacetamide and N,N-diisopropylethylamine (2.9 ml, 16.9 mmol). The reaction mixture was cooled to 0° C. HATU (2.83 g, 7.45 mmol) was added and the reaction mixture was stirred at 0° C. for 1 h. 1-(2-Amino-ethyl)-1H-[1,2,3]triazole-4-carboxylic acid methyl ester hydrochloride (1.4 g, 6.78 mmol) was added and the reaction mixture was stirred at room temperature overnight. The reaction mixture was quenched with 1.0 M HCl and extracted with EtOAc. The organic layer was washed with aqueous $KHCO_3$, water and brine then concentrated and dried under high vacuum. The residue was triturated with diethyl ether to afford 1-[2-(2,3,4-trimethoxy-benzoylamino)-ethyl]-1H-[1,2,3]triazole-4-carboxylic acid methyl ester as a light brown semisolid which was used without further purification.

A flask was charged with 1-[2-(2,3,4-trimethoxy-benzoylamino)-ethyl]-1H-[1,2,3]triazole-4-carboxylic acid methyl ester (2.22 g, 6.1 mmol) and 60 ml methanol. Then, 1.0 M NaOH (24 ml, 24 mmol) was added and the reaction mixture was stirred at room temperature overnight. The reaction mixture was partially concentrated then taken up in water, acidified with 1.0 M HCl and extracted twice with 200 ml EtOAc. The organic layers were combined, dried over sodium sulfate, filtered and concentrated. The residue was taken up in 70 ml dichloromethane, 40 ml EtOAc and 10 ml methanol and then concentrated to a volume of ~30 ml. Diethyl ether was added and the suspension was filtered, rinsed with diethyl ether and dried under high vacuum to afford 1.8 g (84%) 1-[2-(2,3,4-trimethoxy-benzoylamino)-ethyl]-1H-[1,2,3]triazole-4-carboxylic acid as a white solid. LC/HR-MS: $(M+H)^+=351.1293$.

1-[2-(2,3,4-Trimethoxy-benzoylamino)-ethyl]-1H-[1,2,3]triazole-4-carboxylic acid (160 mg, 0.46 mmol), TBTU (161 mg, 0.50 mmol) and (R)-BoroLeu(+)-pinanediol-HCl (138 mg, 0.46 mmol) were suspended in 6 ml dichloromethane at 0° C. N,N-Diisopropylethylamine (0.17 ml, 1.00 mmol) dissolved in 1 ml dichloromethane was added dropwise at 0° over a period of 15 min. The reaction mixture was stirred at 0° C. and at room temperature for 3 h. The reaction mixture was diluted with 50 ml dichloromethane and washed with 50 ml 1M HCl, 50 ml 2M $KHCO_3$ and 50 ml water. The organic layer was dried over sodium sulfate, filtered and concentrated. The residue was chromatographed over 20 g silica gel with EtOAc/dichloromethane (gradient: 0-50% EtOAc). All fractions containing product were combined and concentrated to afford 111 mg (41%) of 1-[2-(2,3,4-trimethoxy-benzoylamino)-ethyl]-1H-[1,2,3]triazole-4-carboxylic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide as a white foam. LC/HR-MS: $(M+H)^+=460.2359$.

1-[2-(2,3,4-Trimethoxy-benzoylamino)-ethyl]-1H-[1,2,3]triazole-4-carboxylic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide (109 mg, 0.18 mmol), isobutylboronic acid (52 mg, 0.51 mmol) and 2N HCl (0.15 ml, 0.30 mmol) were dissolved in 1.5 ml methanol and 1.5 ml heptane. The reaction mixture was stirred at room temperature overnight. The methanolic layer was separated and washed twice with 3 ml heptane. The methanolic layer was treated with 7 ml EtOAc and concentrated. The residue was taken up in 7 ml EtOAc and concentrated. The residue was triturated with diethyl ether. The resulting white solid was extracted with dichloromethane and water. The organic layer was dried over sodium sulfate, filtered and concentrated. The residue was triturated with diethyl ether to afford 21 mg (25%) of (R)-3-methyl-1-(1-(2-(2,3,4-trimethoxybenzamido)ethyl)-1H-1,2,3-triazole-4-carboxamido)butylboronic acid as a white solid. LC/HR-MS: $(M+H)^-=462.2161$.

Example 2

(R)-2-Phenyl-1-(1-(2-(2,3,4-trimethoxybenzamido)ethyl)-1H-1,2,3-triazole-4-carboxamido)ethylboronic acid

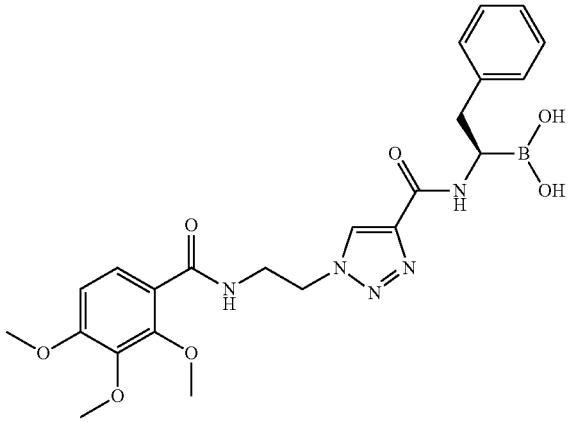 [SMILES: COc1ccc(C(=O)NCCn2cc(C(=O)N[C@@H](Cc3ccccc3)B(O)O)nn2)c(OC)c1OC]

In a 10 ml round-bottomed flask, 1-(2-(2,3,4-trimethoxy-benzamido)ethyl)-1H-1,2,3-triazole-4-carboxylic acid (150 mg, 0.43 mmol) and (R)-BoroPhe-(+)-pinanediol-HCl (158 mg, 0.47 mmol) were dissolved in 3 ml DMF and cooled to 0° C. N,N-Diisopropylethylamine (0.19 ml, 1.09 mmol) was added dropwise at 0° followed by HATU (179 mg, 0.47 mmol). After the addition was complete, the ice bath was removed and the reaction mixture was stirred at room temperature overnight. The reaction was quenched with water and extracted twice with 1:1 diethyl ether/EtOAc (40 ml). The organic layers were washed twice with water and once with brine then combined, dried over sodium sulfate, filtered and concentrated. The residue was purified by chromatography over 25 g silica gel with EtOAc/dichloromethane (gradient: 0-50% EtOAc). All fractions containing product were combined and concentrated to afford 153 mg (57%) 1-[2-(2,3,4-trimethoxy-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide as an off-white foam. LC/MS: (M−H)$^−$=630.

In a 10 ml round-bottomed flask, 1-[2-(2,3,4-trimethoxy-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide (151 mg, 0.24 mmol) and isobutylboronic acid (70 mg, 0.69 mmol) were dissolved in 1.2 ml methanol and 2.4 ml hexanes. 1.0 M Hydrochloric acid (0.60 ml, 0.60 mmol) was added and the reaction mixture was stirred at room temperature overnight. The reaction was diluted with 10 ml methanol and extracted with hexanes. The hexanes layer was back-extracted with 10 ml methanol. The methanolic layers were washed twice with hexanes then combined and concentrated. The residue was dissolved in 20 ml dichloromethane and washed with a mixture of 2 ml water and 2 ml saturated NaHCO$_3$ solution. The aqueous layer was extracted with dichloromethane. The organic layers were combined, dried over sodium sulfate, filtered and concentrated. The residue was purified by chromatography over 4 g silica gel with MeOH/dichloromethane (gradient: 0-10% MeOH then 10% MeOH/chloroform). All fractions containing product were combined and concentrated. The residue was triturated with diethyl ether to afford 24 mg (20%) (R)-2-phenyl-1-(1-(2-(2,3,4-trimethoxybenzamido)ethyl)-1H-1,2,3-triazole-4-carboxamido)ethylboronic acid as a white powder. LC/MS: (M+Na)$^+$=520; $^1$H NMR (400 MHz, CDCl$_3$) □: 8.23 (t, J=5.7 Hz, 1H), 8.18 (s, 1H), 7.88 (d, J=9.0 Hz, 1H), 7.72 (br. s., 1H), 7.18-7.33 (m, 5H), 6.77 (d, J=9.0 Hz, 1H), 4.71 (t, J=5.6 Hz, 2H), 3.98 (d, J=5.6 Hz, 2H), 3.91 (s, 3H), 3.84 (s, 3H), 3.82 (s, 3H), 3.36 (br. s., 1H), 3.06 (dd, J=14.1, 4.8 Hz, 1H), 2.87 (dd, J=14.1, 9.3 Hz, 1H).

Example 3

(R)-1-(1-(2-(2-Fluoro-4-(trifluoromethyl)benzamido)ethyl)-1H-1,2,3-triazole-4-carboxamido)-2-phenyl-ethylboronic acid

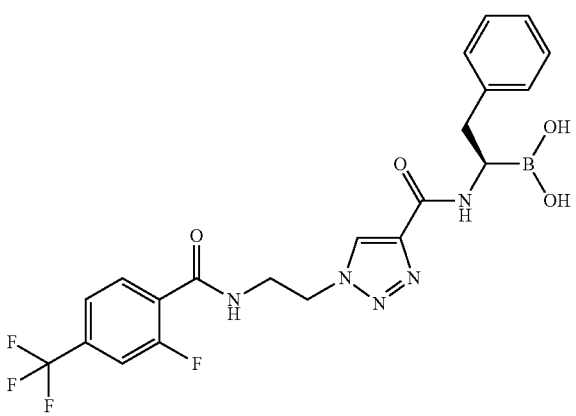 [SMILES: O=C(N[C@@H](Cc1ccccc1)B(O)O)c1cn(CCNC(=O)c2ccc(C(F)(F)F)cc2F)nn1]

2-Fluoro-4-(trifluoromethyl)benzoic acid (2.31 g, 11.1 mmol) was dissolved in 160 ml N,N-dimethylacetamide. N,N-Diisopropylethylamine (4.75 ml, 27.8 mmol) was added, the reaction was cooled to 0° C., and HATU (4.64 g, 12.2 mmol) was added. After 1 h stirring at 0° C., 1-(2-amino-ethyl)-1H-[1,2,3]triazole-4-carboxylic acid methyl ester hydrochloride (2.29 g, 11.1 mmol) was added. The reaction mixture was stirred at room temperature overnight then quenched with 1M HCl and extracted with EtOAc. The organic phase was washed with aqueous KHCO$_3$, water and brine then concentrated. The crude residue was triturated with diethyl ether to afford 2.79 g (70%) 1-[2-(2-fluoro-4-trifluoromethyl-benzoylamino)-ethyl]-1H-[1,2,3]triazole-4-carboxylic acid methyl ester as an off-white solid. LC/HR-MS: (M+H)$^+$=361.0921.

1-[2-(2-Fluoro-4-trifluoromethyl-benzoylamino)-ethyl]-1H-[1,2,3]triazole-4-carboxylic acid methyl ester (2.79 g, 7.74 mmol) was suspended in 60 ml MeOH. To the thick slurry was added 1.0 M NaOH (31 ml, 31.0 mmol). The reaction mixture was stirred at room temperature overnight during which time the reaction became homogeneous. The MeOH was evaporated then the residue was taken up in water, acidified with aqueous HCl and extracted twice with EtOAc. The organic layers were combined, dried over sodium sulfate, filtered and concentrated to give a small amount of solid. The aqueous layers were combined, made basic with aqueous NaOH and concentrated. The residue was cooled to 0 C and acidified with conc. HCl. The resultant precipitate was collected via filtration and dried under high vacuum. The two batches were combined to afford 2.0 g (75%) 1-[2-(2-fluoro-4-trifluoromethyl-benzoylamino)-ethyl]-1H-[1,2,3]triazole-4-carboxylic acid as a white solid. LC/HR-MS: (M+H)$^+$=347.0760.

In a 10 ml round-bottomed flask, 1-(2-(2-fluoro-4-(trifluoromethyl)benzamido)ethyl)-1H-1,2,3-triazole-4-carboxylic acid (125 mg, 0.36 mmol) and (R)-BoroPhe-(+)-pinanediol-HCl (133 mg, 0.40 mmol) were dissolved in 2.5 ml DMF and cooled to 0° C. N,N-Diisopropylethylamine (0.16 ml, 0.92 mmol) was added dropwise at 0° followed by HATU (151 mg, 0.40 mmol). After the addition was complete, the ice bath was removed and the reaction mixture was stirred at room temperature overnight. The reaction was quenched with water and extracted twice with 1:1 diethyl ether/EtOAc (40 ml). The organic layers were washed twice with water and once with brine then combined, dried over sodium sulfate, filtered and concentrated. The residue was purified by chromatography over 25 g silica gel with EtOAc/dichloromethane (gradient: 0-40% EtOAc). All fractions containing product were combined and concentrated to afford 124 mg (49%) of 1-[2-(2-fluoro-4-trifluoromethyl-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide as a colorless oil. LC/MS: (M−H)$^−$=626.

In a 10 ml round-bottomed flask, 1-[2-(2-fluoro-4-trifluoromethyl-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide (117 mg, 0.17 mmol) and isobutylboronic acid (50 mg, 0.49 mmol) were dissolved in 0.8 ml methanol and 1.6 ml hexanes. 1.0 M Hydrochloric acid (0.42 ml, 0.42 mmol) was added and the reaction mixture was stirred at room temperature overnight. The reaction was diluted with 10 ml methanol and extracted with hexanes. The hexanes layer was back-extracted with 10 ml methanol. The methanolic layers were washed twice with hexanes then combined and concentrated. The residue was dissolved in 20 ml dichloromethane and washed with a mixture of 2 ml water and 2 ml saturated NaHCO$_3$ solution. The aqueous layer was extracted with dichloromethane. The organic layers were combined, dried over sodium sulfate, filtered and concentrated. The residue was purified by chromatography over 4 g silica gel with MeOH/chloroform (gradient: 0-10% MeOH, then 10% MeOH/EtOAc). All fractions containing product were combined and concentrated. The residue was triturated with diethyl ether to afford 19 mg (21%) of (R)-1-(1-(2-(2-fluoro-4-(trifluoromethyl)benzamido)ethyl)-1H-1,2,3-triazole-4-carboxamido)-2-phenylethylboronic acid as an off-white powder. LC/MS: (M+Na)$^+$=516; $^1$H NMR (400 MHz, CDCl$_3$) □: 8.21 (br. s., 1H), 8.02 (t, J=7.6 Hz, 1H), 7.77 (br. s., 1H), 7.41 (d, J=8.1 Hz, 1H), 7.06-7.30 (m, 7H), 4.55-4.63 (m, 2H), 3.92 (d, J=4.5 Hz, 2H), 3.22 (br. s., 1H), 2.90-2.98 (m, 1H), 2.71-2.82 (m, 1H).

Example 4

(R)-1-(1-(2-(2-Methoxy-4-(trifluoromethyl)benzamido)ethyl)-1H-1,2,3-triazole-4-carboxamido)-2-phenylethylboronic acid

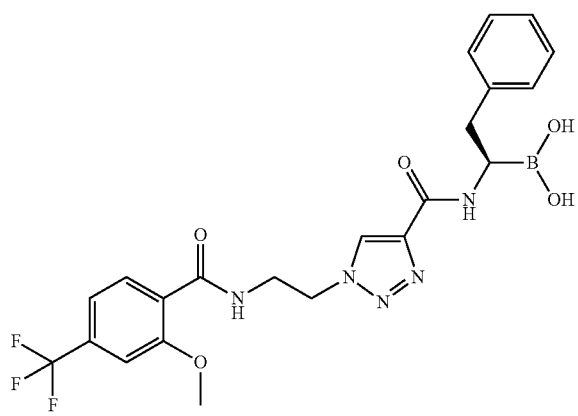 [SMILES: COc1cc(C(F)(F)F)ccc1C(=O)NCCn1cc(C(=O)N[C@@H](Cc2ccccc2)B(O)O)nn1]

In a 50 ml round-bottomed flask, 1-(2-tert-butoxycarbonylamino-ethyl)-1H-[1,2,3]triazole-4-carboxylic acid methyl ester (500 mg, 1.85 mmol) was suspended in 7 ml dichloromethane. Trifluoroacetic acid (4.0 ml, 52 mmol) was added slowly which caused all solids to dissolve. The reaction mixture was stirred at room temperature for 2.5 h then concentrated and dried under high vacuum. The residue was dissolved in 5 ml DMF and 2-methoxy-4-(trifluoromethyl) benzoic acid (390 mg, 1.77 mmol) was added. N,N-Diisopropylethylamine (1.5 ml, 8.6 mmol) was added dropwise followed by HATU (741 mg, 1.95 mmol). The reaction mixture was stirred at room temperature overnight then quenched with water and diluted with petroleum ether. The resultant suspension was filtered, rinsing with water and a little petroleum ether then dried under high vacuum to afford 557 mg (84%) of 1-[2-(2-methoxy-4-trifluoromethyl-benzoylamino)-ethyl]-1H-[1,2,3]triazole-4-carboxylic acid methyl ester as an off-white solid. LC/MS: (M+H)$^+$=373; $^1$H NMR (400 MHz, CDCl$_3$) □: 8.30 (dd, J=8.1, 0.8 Hz, 1H), 8.19 (br. s., 1H), 8.14 (s, 1H), 7.37 (dd, J=8.1, 0.8 Hz, 1H), 7.20 (s, 1H), 4.69-4.76 (m, 2H), 4.02-4.09 (m, 2H), 4.00 (s, 3H), 3.98 (s, 3H).

In a 50 ml round-bottomed flask, 1-[2-(2-methoxy-4-trifluoromethyl-benzoylamino)-ethyl]-1H-[1,2,3]triazole-4-carboxylic acid methyl ester (555 mg, 1.49 mmol) was suspended in 3 ml methanol and 30 ml THF. Lithium hydroxide (161 mg, 6.71 mmol) was added followed by 3 ml water. The reaction mixture was stirred at room temperature overnight then the organic solvents were evaporated. The aqueous residue was cooled to 0° C. and acidified with 1.0 M HCl until pH-2 which caused a precipitate to form. The suspension was filtered and washed with water then dried under high vacuum to give 452 mg (84%) of 1-[2-(2-methoxy-4-trifluoromethyl-benzoylamino)-ethyl]-1H-[1,2,3]triazole-4-carboxylic acid as an off-white solid. LC/MS: (M+H)$^+$=359.

In a 10 ml round-bottomed flask, 1-[2-(2-methoxy-4-trifluoromethyl-benzoylamino)-ethyl]-1H-[1,2,3]triazole-4-carboxylic acid (150 mg, 0.42 mmol) and (R)-BoroPhe-(+)-pinanediol-HCl (155 mg, 0.46 mmol) were dissolved in 2.5 ml DMF and cooled to 0° C. N,N-Diisopropylethylamine (0.19 ml, 1.09 mmol) was added dropwise at 0° followed by HATU (175 mg, 0.46 mmol). After the addition was complete, the ice bath was removed and the reaction mixture was stirred at room temperature overnight. The reaction was quenched with water and extracted twice with 1:1 diethyl ether/EtOAc (40 ml). The organic layers were washed twice with water and once with brine then combined, dried over sodium sulfate, filtered and concentrated. The residue was chromatographed over 25 g silica gel with EtOAc/dichloromethane (gradient: 0-50% EtOAc). All fractions containing product were combined and concentrated to afford 195 mg (66%) of 1-[2-(2-methoxy-4-trifluoromethyl-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide as a colorless oil. LC/MS: (M–H)$^−$=638.

In a 10 ml round-bottomed flask, 1-[2-(2-methoxy-4-trifluoromethyl-benzoylamino)-ethyl]-1H-[1,2,3]triazole-4-carboxylic acid [(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-amide (189 mg, 0.27 mmol) and isobutylboronic acid (78 mg, 0.77 mmol) were dissolved in 1.3 ml methanol and 2.6 ml hexanes. 1.0 M Hydrochloric acid (0.67 ml, 0.67 mmol) was added and the reaction mixture was stirred at room temperature overnight. The reaction was diluted with 10 ml methanol and extracted with hexanes. The hexanes layer was back-extracted with 10 ml methanol. The methanolic layers were washed twice with hexanes then combined and concentrated. The residue was dissolved in 20 ml dichloromethane and washed with a mixture of 2 ml water and 2 ml saturated NaHCO$_3$ solution. The aqueous layer was extracted with dichloromethane. The organic layers were combined, dried over sodium sulfate, filtered and concentrated. The residue was triturated with diethyl ether/EtOAc to afford 51 mg (38%) of (R)-1-(1-(2-(2-methoxy-4-(trifluoromethyl) benzamido)ethyl)-1H-1,2,3-triazole-4-carboxamido)-2-phenylethylboronic acid as a white powder. LC/MS: (M+Na)$^+$=528; $^1$H NMR (400 MHz, CDCl$_3$) □: 8.26 (d, J=8.1 Hz, 1H), 8.14 (s, 1H), 7.97 (t, J=5.7 Hz, 1H), 7.71 (br. s., 1H), 7.34 (dd, J=8.1, 0.9 Hz, 1H), 7.24-7.28 (m, 4H), 7.16-7.23 (m, 1H), 7.14 (s, 1H), 4.70 (t, J=5.4 Hz, 2H), 3.94-4.05 (m, 2H), 3.89 (s, 3H), 3.30-3.40 (m, 1H), 3.07 (dd, J=14.3, 5.1 Hz, 1H), 2.86 (dd, J=14.3, 10.0 Hz, 1H).

Example 5

Assay Protocols and Results

Cell-Based Proteasome Activity/Selectivity Assay

The Cell-Based Proteasome subunit activity/selectivity assay was a panel of 5 fluorogenic assays that independently measured the activity of β5c or β 5i (chymotrypsin-like activity), β 2c/2i (trypsin-like), and β 1c or β 1i (caspase-like) protease activity associated with the proteasome complex in cultured cells. Specifically, the following substrates were used for respective subunit activities: β 1i: (PAL)$_2$ Rh110, β 1c: (LLE)₂Rh110, β 2c/2i: (KQL)₂Rh110, β 5c: (WLA)₂Rh110, β 5i: (ANW)₂Rh110. The following procedure was followed:

Cell preparation: Plated 25 µl of Ramos cells (2×10⁶/ml in DPBS) into half area plate (PerkinElmer Cat 6005569) to final 5×10⁴ cells/well. Added 0.5 µl of 100× 4-fold serial diluted test compounds or DMSO to each well. Highest concentration of compound tested was 20 µM, thus compound serial dilution started from 200 mM. Incubated for 30 minutes at 37° C. Then equilibrated at room temperature for 15 minutes. Added 25 µl of 2× reaction mix consisting of 0.025% digitonin, 20 µM of each substrates and 0.5M sucrose in DPBS. Shaked for one minute @ 700 rpm. Incubated for 120 min at room temperature. Then read the plates with an Envision multilabel plate reader (PerkinElmer) with 500 nm excitation/519 nm emission.

Modified PBMC Proteasome Activity Assay

This cell-based proteasome activity assay was similar to previous Ramos cell-based assay as of the substrates, but using human PBMCs in the context of complete RPMI with 10% FBS as reaction buffer. This assay was designed to assess the level of cellular penetration of test compounds in primary human cells. The following procedure was followed: Fresh isolated PBMC from healthy donor were plated at 1×10⁵ cells/well in 100 µl of complete RPMI with 10% FBS in V bottom 96 plates. Added 1 µl of 100× 4-fold serial diluted compounds/well and incubated for 1 hr. The highest compound concentration tested was 20 µM (100× working stock start with 2 mM). Spun down the cells @ 2000 rpm for 5 min. Removed all supernatant. Then resuspended the cells in 25 µl DPBS and transferred the cells to a fresh half-area plate (PerkinElmer Cat 6005569). In the final reaction volume was 50 µl, including 25 µl cell suspension, 0.5 µl 100× inhibitor or DMSO, 25 µl substrate mix containing 0.025% digitonin, 20 uM substrate (Substrate: (PAL)₂Rh110, (LLE)₂ Rh110, (KQL)₂Rh110, (WLA)₂ Rh110, or (ANW)₂Rh110)/in 10% FBS and 0.5M sucrose mixture. Shaked for one minute (@ 700 rpm). Incubated for 2 hrs, then read the plates with Envision plate reader using 500 nm excitation/519 nm emission.

PBMC IP-10 Assay

PBMCs were isolated from whole blood as follows: Blood was collected in a sterile environment in heparinized tubes. Blood was diluted with an equal volume PBS/2% FCS and 30 ml of this mixture was added to ACCUSPIN tubes containing 15 ml Histopaque-1077 already centrifuged at 800 g for 30 seconds and warmed up at room temperature. The tubes were then centrifuged at 800 g for 20 minutes at room temperature with no brake. The mononuclear band, just above the polyethylene frit, was removed by Pasteur pipet. These mononuclear cells were washed three times with sterile PBS, counted, and resuspended in RPMI 1640 supplemented with 10% heat inactivated fetal calf serum, 10 mM HEPES, 1 mM sodium pyruvate, penicillin (50 U/ml), streptomycin (50 µg/ml) and glutamine (2 mM) to approximately 1.5×10⁶/ml. Approximately 2×10⁵ cells/well were plated in 96 well tissue culture plates (BD Falcon 353072), and preincubated 60 mi/37° C. with a titration of compounds, in a final concentration of 1% DMSO. Cells were then stimulated with CpG Type A (Invivogen, Cat # tlrl-2216; ODN 2216) at a final concentration of 2.5 µM. Cells were incubated overnight, and supernatants were removed. PBMC viability of cells remaining in the well was measured with ATPlite luminescence assay (Perkin-Elmer) per the manufacturer's instructions. Luminescence was measured on the Perkin-Elmer Envision, using the luminescence filter. IP10 level was measured with CXCL10/IP10 AlphaLISA kit (Perkin-Elmer) per the manufacturer's instructions, except halving all volumes. Fluorescence was measured on the Envision Multilabel plate reader, using the AlphaScreen standard settings.

Results:

The results of the above assays for representative compounds of the invention are provided in Table 1 below, wherein the IC50 and EC50 activity values are in µM:

TABLE 1

| Example No. | Ic50: ramos:ac-(anw)2-r110 | Ic50: ramos:rh110-(wla)2 | Ic50: ramos:rh110-(kql)2 | Ic50: ramos:rh110-(pal)2 | Ic50: ramos:rh110-(lle)2 | Ec50 |
|---|---|---|---|---|---|---|
| 1 | 0.002 | 0.039 | 20 | 0.004 | 0.32 | 0.0295 |
| 2 | 0.007 | 0.016 | 13.524 | 0.025 | 6.632 | 0.03367 |
| 3 | 0.002 | 0.006 | 20 | 0.01 | 7.345 | 0.0268 |
| 4 | 0.002 | 0.02 | 20 | 0.009 | 7.485 | 0.01225 |

It is to be understood that the invention is not limited to the particular embodiments of the invention described above, as variations of the particular embodiments may be made and still fall within the scope of the appended claims.

The invention claimed is:

1. A compound of formula (I):

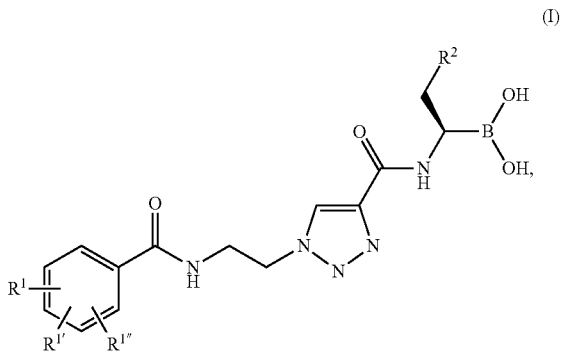

wherein:
R¹, R¹' and R¹'', of each other, are hydrogen, alkoxy, halogen or —CF₃; and
R² is C₁₋₇ alkyl or phenyl,
or a pharmaceutically acceptable salt thereof.

2. The compound according to claim 1, wherein R¹, R¹' and R¹'', independently of each other, are hydrogen, methoxy, fluorine or —CF₃.

3. The compound according to claim 1, wherein one of R¹, R¹' or R¹'' is hydrogen and the other two, independently of each other, are alkoxy, halogen or —CF₃.

4. The compound according to claim 1, wherein one of $R^1$, $R^{1'}$ or $R^{1''}$ is hydrogen and the other two, independently of each other, are methoxy, fluorine or —$CF_3$.

5. The compound according to claim 1, wherein $R^2$ is methyl.

6. The compound according to claim 1, wherein $R^2$ is phenyl.

7. The compound according to claim 1, wherein said compound is:
- (R)-3-Methyl-1-(1-(2-(2,3,4-trimethoxybenzamido)ethyl)-1H-1,2,3-triazole-4-carboxamido)butylboronic acid;
- (R)-2-Phenyl-1-(1-(2-(2,3,4-trimethoxybenzamido)ethyl)-1H-1,2,3-triazole-4-carboxamido)ethylboronic acid;
- (R)-1-(1-(2-(2-Fluoro-4-(trifluoromethyl)benzamido)ethyl)-1H-1,2,3-triazole-4-carboxamido)-2-phenylethylboronic acid;
- (R)-1-(1-(2-(2-Methoxy-4-(trifluoromethyl)benzamido)ethyl)-1H-1,2,3-triazole-4-carboxamido)-2-phenylethylboronic acid; or
- pharmaceutically acceptable salts thereof.

8. A pharmaceutical composition, comprising a therapeutically effective amount of a compound according to claim 1 and a pharmaceutically acceptable carrier.

* * * * *